(12) United States Patent
Eppelmann et al.

(10) Patent No.: US 9,523,083 B2
(45) Date of Patent: Dec. 20, 2016

(54) BIOCHEMICAL SYNTHESIS OF 1,4-BUTANEDIAMINE

(75) Inventors: Katrin Eppelmann, Kalamazoo, MI (US); Petrus M. M. Nossin, Nederweert (NL); Susanne M. Kremer, Linnich-Gereonsweiler (DE); Marcel G. Wubbolts, Sittard (NL)

(73) Assignee: DSM IP ASSETS B.V., Heerlen (NL)

( * ) Notice: Subject to any disclaimer, the term of this patent is extended or adjusted under 35 U.S.C. 154(b) by 1740 days.

(21) Appl. No.: 11/632,625

(22) PCT Filed: Jul. 11, 2005

(86) PCT No.: PCT/EP2005/007608
§ 371 (c)(1),
(2), (4) Date: Jan. 18, 2008

(87) PCT Pub. No.: WO2006/005604
PCT Pub. Date: Jan. 19, 2006

(65) Prior Publication Data
US 2009/0275093 A1    Nov. 5, 2009

(30) Foreign Application Priority Data
Jul. 15, 2004 (EP) .................... 04077047

(51) Int. Cl.
| C12P 21/00 | (2006.01) |
| C12N 15/09 | (2006.01) |
| C12N 1/21 | (2006.01) |
| C12N 9/10 | (2006.01) |
| C12N 9/88 | (2006.01) |
| C12P 13/00 | (2006.01) |

(52) U.S. Cl.
CPC .............. *C12N 9/1029* (2013.01); *C12N 9/88* (2013.01); *C12P 13/001* (2013.01); *Y02P 20/52* (2015.11)

(58) Field of Classification Search
CPC ......... C12N 9/1029; C12N 9/88; C12P 12/001
USPC .......................... 435/69.1, 69.2, 106, 252.33
See application file for complete search history.

(56) References Cited

FOREIGN PATENT DOCUMENTS

| EP | 0723240 A | 8/1996 |
| WO | WO 99/46363 * | 9/1999 |
| WO | 01/11062 A2 | 2/2001 |
| WO | 03/050296 A2 | 6/2003 |

OTHER PUBLICATIONS

Hannig et al. 1998, Trends in Biotechnology Strategies for optimizing heterologous protein expression in *Escherichia coli* vol. 16, Issue 2, Feb. 1, 1998, pp. 54-60.*
The Five Kingdoms of Life// http://waynesword.palomar.edu/trfeb98.htm pp. 1-17, last visited Nov. 11, 2014.*
Qian et al Metabolic Engineering of *Escherichia coli* for the Production of Putrescine: A Four Carbon Diamine Biotechnology and Bioengineering, vol. 104, No. 4, Nov. 1, 2009 pp. 651-662.*
Pienkos et al Role of pretreatment and conditioning processes on toxicity of lignocellulosic biomass hydrolysates Cellulose (2009) 16:743-762.*
*Saccharomyces cerevisiae* From Wikipedia, the free encyclopedia, last visited on Jan. 13, 2016.*
*Escherichia coli* From Wikipedia, the free encyclopedia, last visited on Jan. 13, 2016.*
Corynebacterium From Wikipedia, the free encyclopedia,last visited on Jan. 13, 2016.*
Sedlak et al., Expression of *E. coli* araBAD operon encoding enzymes for metabolizing L-arabinose in *Saccharomyces cerevisiae* Enzyme and Microbial Technology 28 (2001) 16-24.*
International Search Report for PCT/EP2005/007608 mailed Nov. 7, 2005.
McCrae et al., "Complementation of a polyamine-deficient *Escherichia coli* mutant by expression of mouse ornithine decarboxylase" Molecular and Cellular Biology, vol. 7, No. 1, pp. 564-567 (1987).
Gupta et al., "Effect of spermidine on the in vivo degradation of ornithine decarboxylase in *Saccharomyces cerevisiae*" Proceedings of the National Academy of Sciences of the United States of America, vol. 98, No. 19, pp. 10620-10623 (2001).
Panagiotidis et al., "Relationship of the expression of the S20 and L34 ribosomal proteins to polyamine biosynthesis in *Escherichia coli*" International Journal of Biochemistry & Cell Biology, vol. 27, No. 2, pp. 157-168, (1995).
Klein et al., "*Haemonchus contortus*: Cloning and functional expression of a cDNA encoding ornithine decarboxylase and development of a screen for inhibitors" Experimental Parasitology, vol. 87, No. 3, pp. 171-184 (1997).
Fonzi et al., "Expression of the gene for ornithine decarboxylase of *Saccharomyces cerevisiae* in *Escherichia coli*" Molecular and Cellular Biology, vol. 5, No. 1, pp. 161-166 (1985).
Pantoja-Hernandez et al., "Expression of ornithine decarboxylase of *Coccidioides immitis* in three *Escherichia coli* strains carrying the lambda DE3 lysogen and *E. coli* EWH319 strain odc-null mutant" Biotechnology Letters, vol. 26, No. 1, pp. 75-78 (2004).
Niemann et al., "*Panagrellus redivivus* ornithine decarboxylase: Structure of the gene, expression in *Escherichia coli* and characterization of the recombinant protein" Biochemical Journal, vol. 317, No. 1, pp. 135-140 (1996).

(Continued)

*Primary Examiner* — Maria Leavitt
(74) *Attorney, Agent, or Firm* — Nixon & Vanderhye P.C.

(57) ABSTRACT

Process for biochemical synthesis of 1,4-butanediannine in a microorganism having an increased level of an ornithine decarboxylase activity as compared to the native level of the ornithine decarboxylase activity, in which the increased ornithine decarboxylase activity is obtained by overexpression of an ornithine decarboxylase encoding gene with increased translational and/or transcriptional efficiency. The process is performed by excreting 1,4-butanediamine produced in the microorganism into a fermentation broth, and recovering the 1,4-butanediannine from the fermentation broth. The increased translational and/or transcriptional efficiency is obtained by the use of a strong, regulated promoter consisting of an isopropvl-B-D-thiogalactoside (IPTG) inducible strong promoter.

2 Claims, No Drawings

(56) References Cited

OTHER PUBLICATIONS

Michael et al., "Molecular cloning and functional identification of a plant orninthine decarboxylase cDNA" Biochemical Journal, vol. 314, No. 1, pp. 241-248 (1996).

Craig et al., "High level expression in *Escherichia coli* of soluble, enzymatically active schistosomal hypoxanthine/guanine phosphoribosyltransferase and trypanosomal ornithine decarboxylase" Proceedings of the National Academy of Sciences of the United States of America, vol. 88, No. 6, pp. 2500-2504 (1991).

Phillips et al., "*Trypanosoma brucei* ornithine decarboxylase: enzyme purification, characterization, and expression in *Escherichia coli*" Journal of Biological Chemistry, vol. 263, No. 34, pp. 17933-17941 (1988).

Klein et al., "Reconstitution of a bacterial/plant polyamine biosynthesis pathway in *Saccharomyces cerevisiae*" Microbiology, vol. 145, No. 2, pp. 301-307 (1999).

Kashiwagi et al., "Adjustment of polymine contents in *Escherichia coli*" Journal of Bacteriology, vol. 170, No. 7, pp. 3131-3135 (1988).

Boyle et al., "Expression of the cloned gene encoding the putrescine biosynthetic enzymes and methionine adenosyltransferase of *Escherichia coli* (speA, speB, spec and metK)" Gene, vol. 30, No. 1-3, pp. 129-136 (1984).

Kashiwagi et al., "Coexistence of the genes for putrescine transport protein and ornithine decarboxylase at 16 min on *Escherichia coli* chromosome" Journal of Biological Chemistry, vol. 266, No. 31, pp. 20922-20927 (1991).

Nakada et al., "Identification of the putrescine biosynthetic genes in *Pseudomonas aeruginosa* and characterization of agmatine deiminase and N-carbamoylputrescine amidohydrolase of the arginine decarboxylase pathway" Microbiology, vol. 149, No. 3, pp. 707-714 (2003).

Cunin et al., "Biosynthesis and metabolism of arginine in bacteria" Microbiological Reviews, vol. 50, No. 3, pp. 314-352 (1986).

Tabor et al., "Polyamines in microorganisms" Microbiological Reviews, vol. 49, No. 1, pp. 81-99 (1985).

Cohen, *A Guide to the Polyamines—Biosynthesis and Metabolism of Diamines in Bacteria*, Oxford University Press, pp. 122-183 (1998).

Fukuchi et al., "Decrease in cell viability due to the accumulation of spermidine in spermidine acetyltransferase-deficient mutant of *Escherichia coli*" Journal of Biological Chemistry, vol. 270, No. 32, pp. 18831-18835 (1995).

Suzuki et al., "Antizyme protects against abnormal accumulation and toxicity of polyamines in ornithine decarboxylase-overproducing cells" Proceedings of the National Academy of Sciences of the United States of America, vol. 91, No. 19, pp. 8930-8934 (1994).

\* cited by examiner

SEQUENCE LISTING

<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: primer -continued

```
<400> SEQUENCE: 1
gagctctaga ccagtttgac ccatatct                                          28

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
ttttgcatgc ttacttcaac acataaccgt ac                                     32

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gagctctaga ccagtttgag gaatatct                                          28

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
gacctgctgg tacctaaaat aaagagatga aa                                     32

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
tcgatctaga ctgactcata attttteccc                                        30

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6
acactttcta gaataatttg aggttcgcta tg                                     32

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
catggcatgc ggtgcttact cg                                                22
```

BIOCHEMICAL SYNTHESIS OF 1,4-BUTANEDIAMINE

This application is the US national phase of International Patent Application No. PCT/EP2005/007608 filed 11 Jul. 2005, which designated the U.S. and claimed priority of EP 04077047.1 filed 15 Jul. 2004; the entire contents of each of which are hereby incorporated by reference.

The present invention relates to a new process for biochemical synthesis of 1,4-butanediamine (CAS number 110-60-1; a compound also referred to as tetramethylenediamine; in biochemical literature it is also being referred to as putrescine) in a microorganism having an increased level of an ornithine decarboxylase activity as compared to the native level of the ornithine decarboxylase activity. Ornithine decarboxylase hereinafter also will be referred to as "ODC". An "increased level of ornithine decarboxylase activity" is hereinafter also referred to as "increased ODC activity". Generally microorganisms having ODC activity are known to be capable of producing polyamines such as spermidine and spermine, which are the common names for respectively the products N-(3-aminopropyl)-1,4-butanediamine and N,N'-bis-(3-aminopropyl)-1,4-butanediamine. Such compounds, as well as various short linear diamines themselves such as, for instance, 1,4-butanediamine and 1,5-pentanediamine (also referred to as cadaverine), are often referred to in biochemical studies as polyamines, even though from a strictly chemical definition of polyamines a higher number of amino groups would be expected. For the purposes of the present patent application, however, the term polyamines is being used in its biochemical meaning and therefore includes 1,4-butanediamine.

The compound 1,4-butanediamine is an important raw material for the production of some of the major engineering plastics: polyamide-4,6, either in the form of a homopolymer, or copolymerised, for example, with about 5 wt. % of polyamide-6 monomer (caprolactam). The homopolymer polyamide-4,6 (nylon-4,6) was described as early as 1938 (U.S. Pat. No. 2,130,948, Carothers). It is the polycondensation product of the monomers 1,4-butanediamine and adipic acid. Presently, especially compounds of polyamide-4,6 are being produced and sold by DSM in the Netherlands under the trade name STANYL®.

For the synthesis of 1,4-butanediamine a number of chemical routes are known. All these chemical routes suffer from the disadvantage that starting materials have to be obtained form sources that are considered to be non-renewable. There exists, however, a substantial need for providing new and feasible routes for the synthesis of 1,4-butanediamine starting from renewable carbon sources and using biochemical processes (also referred to as "biotransformation") in living cells. In general, polyamines are considered to be toxic for any cell or microorganism used in biochemical production. Therefore, until now such new routes by biochemical synthesis, however, were believed to be unattractive.

This can for instance be seen from the following references: Fukuchi et al., J. Biol. Chem., Vol. 270 (1995), pages 18831-18835; and Suzuki et al., Proc. Natl. Acad. Sci. USA, Vol. 91 (1994), pages 8930-8934.

Fukuchi clearly describes the decrease in cell viability (and of synthesis of almost all kinds of proteins) due to the accumulation of spermidine in spermidine acetyltransferase-deficient cells of E. coli (i.e. in cells lacking the acetyltransferase SpeG). Spermidine is a product that is being produced in cells from 1,4-butanediamine as an intermediate. Accordingly, biosynthesis of 1,4-butanediamine inevitably also leads to formation of spermidine.

Suzuki on the one hand also demonstrates (in mice cells), that overproduction of ODC results in accumulation of polyamines, especially of spermidine, and that—upon addition of small amounts of spermidine—already cell death is observed even in cells that are not deficient in speG.

It is to be noticed that Limsuwum et al. (J. Bacteriol. Vol. 182 (2000), pages 5373-5380)have shown that at low temperatures such problems can be overcome by overexpression of the dedicated gene speG. Suzuki et al., (cited above) suggest that the lowered cell viability is due to an insufficient feedback inhibition of ornithine decarboxylase (ODC) by antizymes and can be overcome by overproduction of a suitable antizyme. Such overproduction of antizymes then also would lower the production of polyamines in the cells and is therefore not feasible for 1,4-diaminobutane (DAB) production.

Further, as Kashiwagi et al. described in J. Bacteriol. Vol. 170 (1988), pages 3131-3135, the contents of polyamines in E. coli can be adjusted by overexpression of an ornithine decarboxylase (ODC) encoding gene, in particular of the constitutively expressed speC. For their experiments the plasmid pODC as produced by Boyle et al., (Methods in Enzymology, Vol. 94 (1983), pages 117-121, was used in the cloning. As taught by Kashiwagi et al., even a 70-fold overproduction of ornithine decarboxylase SpeC under the native transcriptional and translational control (i.e. using the native genetic elements consisting of ribosomal binding site and promoter) did only lead to slightly increased levels of the sum of intra- and extracellular 1,4-butanediamine content. As can be seen in the cited Kashiwagi reference, the said authors were unable to reach higher production levels of 1,4-butanediamine than about 25 mg/l (without ornithine feeding). Moreover, they showed that overproduction of ODC in the cells did lead to a strong decrease in ornithine content in the cells (from about 65 μmol/l to less than 1 μmol/l) and concluded that the cells became ornithine deficient when ODC was overproduced. Kashiwagi et al. tried to remove the observed limitation in ornithine content by external feeding of ornithine, but—although a slight improvement was reached—production levels of 1,4-butanediamine did not get higher than about 30 mg/l. Due to the described restriction of the precursor supply by ODC overproduction and because, moreover, it would be expected that higher levels of proteins like ODC would cause increasing effects of toxicity in the cells due to the presence of higher amounts of polyamines, the skilled man, in view of the above references, would assume, that it would be impossible to provide biochemical synthesis processes for the production of 1,4-butanediamine at significantly higher levels than 30 mg/l.

EP-A-0726240 until now is one of the very few patent references relating to the biochemical synthesis of polyamines, including 1,4-butanediamine. However, it describes the production of, inter alia, 1,4-butanediamine by fermentation of natural products containing proteins as a major component. In said process, the natural products first are treated by subjecting them to partial or total degradation, and any undesirable compounds (e.g. Hg, Cr, As, Cd, Se and Pb), cell growth inhibitors, pesticides, antibiotics, detergents, soaps, fats, oils, cyanides and phenols are then removed before the fermentation step. The putrescine and other diamines produced in such a way are being (re-)used as fertilizers and manures, but contain such large number of other substances that they are unsuitable as a raw material for the production of, for example, polyamide-4,6.

Accordingly, there remains a need for an efficient biosynthetic route for the synthesis of 1,4-butanediamine at significantly higher titers than about 30 mg/l, preferably even without the need for external feeding of (expensive) ornithine. This need for improved availability of 1,4-butanediamine mainly is based on its intended use as a starting material, for instance, for the production of polyamide-4,6. In general, the routes to 1,4-butanediamine as are known until today are quite laborious and troublesome, and may lead to a quality of said product which—without further purification—is difficult to be used in the production of nylons. The known chemical routes to 1,4-butanediamine require relatively expensive starting materials and reactants (including reactants that are difficult to handle), and relatively severe reaction conditions of temperature and pressure in a multi-step and multi-reactor design, as well as the use of expensive catalyst systems. Accordingly there remains a need for alternative routes to 1,4-butanediamine, preferably from much less expensive raw materials and avoiding problems of handling reactants like hydrocyanic acid. It is well known that naturally growing, and thus renewable, materials from agricultural production are the basis for carbon sources such as glucose (or other appropriate carbon sources and mixtures thereof) that can be used in fermentation. Such renewable materials are relatively cheap and abundantly available. In general, it is considered to be very advantageous if renewable materials can be used as starting materials for all kinds of chemical materials.

It is thus an aim of the present invention to provide improved possibilities for large-scale industrial production of 1,4-butanediamine by biotransformation.

The present inventors surprisingly have found that this aim is achieved with a new process for biochemical synthesis of 1,4-butanediamine in a microorganism having an increased level of an ornithine decarboxylase activity (increased ODC activity) as compared to the native level of ornithine decarboxylase activity, wherein the increased ornithine decarboxylase activity is obtained by means of overexpression of an ornithine decarboxylase encoding gene with increased transcriptional and/or translational efficiency, and that 1,4-butanediamine produced in such microorganism by biotransformation is excreted into a fermentation broth, and is recovered from the fermentation broth.

According to the present invention, thus, an improved biochemical process for the synthesis of 1,4-butanediamine is provided, and the resulting 1,4-butanediamine is excellently suitable as raw material, for instance, for the production of polyamide-4,6.

As meant in the present patent application, the term "biochemical synthesis" (a term that, in the context of this patent application, alternatively is referred to as "biotransformation") includes not only processes which involve—besides a number of purely chemical reaction steps—one or more biocatalytic reactions using whole cells of suitable production strains, but also purely biochemical processes using whole cells of suitable production strains. Such purely biochemical processes, respectively, are referred to as fermentations in case the biochemical synthesis starts from a suitable carbon source, or are referred to as precursor fermentations in case the biosynthesis starts from an intermediate product already having a carbon skeleton from which the target molecule to be synthesized can be obtained. The processes may be carried out either under aerobic or under anaerobic conditions.

The biocatalytic reactions in the biochemical synthesis of the present invention can be carried out either in vivo or in vitro. Generally, in vivo processes are processes carried out when using living cells (the term "living cells" thereby also including so-called resting cells); in vitro processes, on the other hand, usually are being carried out using cell lysates or (partly) purified enzymes. The biochemical synthesis according to the present invention is carried out in a microorganism. This can be done using whole cells of suitable production strains, but also may be carried out using permeabilized cells; the differentiation between in vivo and in vitro, however, does not make much sense for processes being carried out with permeabilized cells or immobilized host cells. It will be evident, however, that individual biocatalytic steps from the process of the invention, when carried out, for instance, by using immobilized enzymes, etc. are considered equivalent to such steps in the biochemical synthesis as meant in the context of the present application.

Ornithine decarboxylases (i.e. enzymes having ornithine decarboxylation activity, or ODCs) are enzymes classified in class E.C. 4.1.1.17. The level of activity of an ornithine decarboxylase, if overproduced, can easily be compared with the native (i.e. non-overproduced) level of ornithine decarboxylase activity under standard conditions (at 37° C. in the presence of ornithine and PLP) within cell free extracts using the Sigma Diagnostics carbon dioxide detection kit (Sigma); assay described in Osterman, A. L. et al. 1994, Biochemistry 33, p. 13662-13667. The skilled man, accordingly, can easily establish whether the ODC used has an increased level of ornithine decarboxylase activity (increased ODC activity) based on increased translational and/or transcriptional efficiency as compared to the native level of the ornithine decarboxylase activity in the microorganism used by determination of the protein content, or by determining the RNA level. Various standard procedures for determination of protein content, for instance colorimetric as well as spectroscopic methods, are described in Lottspeich and Zorbas, Bioanalytik, Spektrum Akademischer Verlag GmbH, Heidelberg/Berlin, ISBN 3-8274-0041-4 (1998), Chapters 3, 5, 21, 22 and 24. Methods for determination of protein level as well as RNA level, for instance northern hybridization, RT-PCR, and many other methods, are described in J. Sambrook, E. F. Fritsch and T. Maniatis, Molecular Cloning, A Laboratory Manual, $2^{nd}$ Edition, Cold Spring Harbor Laboratory Press, ISBN 0-87969-309-6 (1989). Many other standard procedures, however, are known to the skilled man in this analytic field and do not need to be mentioned here.

Suitable ornithine decarboxylases that can be used in the process of the invention are all enzymes and mutants thereof, that are capable of decarboxylating ornithine. Any such enzyme may be used in the process of the invention, at an increased level of activity, i.e. in overproduced form by means of overexpressing an ornithine decarboxylase gene with increased transcriptional and/or translational efficiency. In addition it is to be noticed, that the term "increased level of activity" as used herein for any specifically named enzyme activity is also intended to encompass such situations where the activity of such enzyme activity, for instance an ornithine decarboxylase, is not present at all in the natural source of the microorganism wherein the reaction is taking place, but is introduced therein purposively by genetic modification with increased transcriptional and/or translational efficiency.

As mentioned above, in the biochemical synthesis of 1,4-butanediamine any ODC enzyme may be used, of which the increased ODC activity, is obtained by means of overexpression of an ODC encoding gene with increased translational and/or transcriptional efficiency. Preferably, the increased translational and/or transcriptional efficiency is obtained by the use of a strong, regulated promoter, preferably by use of a strong inducible promoter.

Most preferably, the increased translational and/or transcriptional efficiency is obtained by the use of an isopropyl-β-D-thiogalactopyranoside (IPTG) inducible strong promoter. Suitable strong promoters are described in J. Sambrook, E. F. Fritsch and T. Maniatis, Molecular Cloning, A Laboratory Manual, 2$^{nd}$ Edition, Cold Spring Harbor Laboratory Press, ISBN 0-87969-309-6 (1989).

In particular, the increased translational and/or transcriptional efficiency is obtained by the use of a promoter selected from the group consisting of T7, T5, ptac, and plac promoters. It will be clear to the man skilled in the art, that the optimum choice of the promoter will be dependent of the host to be used and the reaction conditions to be applied.

In a very preferred embodiment of the invention, the ornithine decarboxylase encoding gene has a Ribosomal Binding Site (RBS) located up-stream of the coding region of the said gene which RBS is adapted to achieve better recognition of RNA-template by the ribosomes. Adaptation of the RBS may be done by any method known to the skilled man, and will take into account specific properties of the host used, etc.

Most preferably, the overexpressed ornithine decarboxylase encoding gene is an ornithine decarboxylase speF or speC gene (each belonging to E.C. 4.1.1.17). Until now SpeC has been investigated in literature much more than SpeF. Most surprisingly, however, and most preferably, best results according to the present invention are achieved when it is an ornithine decarboxylase speF gene.

It is particularly preferred that the overexpressed ornithine decarboxylase encoding gene used in the process according to the invention is an ornithine decarboxylase gene speF or speC originating from one of the genera selected from the group consisting of *Escherichia, Shigella, Salmonella, Yersinia*, and *Shewanella*. The ornithine decarboxylase speF is an inducible ornithine decarboxylase; ornithine decarboxylase speC is a constitutive ornithine decarboxylase.

More preferably, the overexpressed ornithine decarboxylase encoding gene is an ornithine decarboxylase gene originating from one of the species selected from the group consisting of *Escherichia coli, Shigella flexneri, Salmonella typhimutium, Yersinia pestis*, and *Shewanella oneidensis*. Most preferably, the overexpressed ornithine decarboxylase encoding gene is speF originating from one of the species selected from the group consisting of *Escherichia coli, Salmonella typhimutium*, and *Shewanella oneidensis*. When compared to results with overexpression of the constitutive ornithine decarboxylase encoding gene speC, by far the best results according to the present invention indeed are being achieved when using speF.

According to the present invention, in particular, all ornithine decarboxylases can be used that have sufficient, i.e. at least 30%, more preferably at least 45%, and most preferably at least 65% identity with the ODC from the *E. coli* reference enzyme, and are capable of catalyzing the ornithine decarboxylation reaction. Many ODCs are known having such relatively high level of identity with the *E. coli* reference enzyme.

Determining identity percentages with reference enzymes can be performed by methods known to the skilled man, for instance by using the protein sequence of the reference enzyme as a "query sequence" to perform a search against public databases to, for example, identify other family members or related sequences. Such searches can be performed using BLAST programs (version 2.2) using the default parameters of respective program. See httpcolonforwardslashforwardslashwwwdotncbidotnlmdotnihdotgov.

According to the present invention, thus, an improved biochemical process for the synthesis of 1,4-butanediamine is provided, and the resulting 1,4-butanediamine is excellently suitable as raw material for the production of polyamide-4,6 and/or other polyamides.

It will be clear, that—in the context of the present invention—any gene being homologous with any of the genes coding for the abovementioned ornithine decarboxylases and coding for enzymes having ornithine decarboxylase activity sufficiently comparable to the ornithine decarboxylases shown, is to be considered an equivalent thereof and suitable in the process of the invention. Such equivalent genes can suitably be obtained by means of any appropriate cloning strategy known to the skilled man, for instance, by the methods described in the experimental part hereof. Alternatively, such equivalent ornithine decarboxylase genes can also be obtained by purposive construction.

In a further preferred embodiment of the present invention, the process for the biochemical synthesis of 1,4-butanediamine is carried out in a microorganism wherein, additionally to the increased ODC activity also increased enzyme activity is obtained for at least two other enzymes by means of overexpression of either
(i) an arginine decarboxylase encoding gene speA (belonging to E.C. 4.1.1.19) and an agmatinase encoding gene speB (belonging to E.C. 3.5.3.11; also referred to as agmatine ureahydrolase encoding gene); or
(ii) an arginine decarboxylase encoding gene speA (belonging to E.C. 4.1.1.19), and an agmatine iminohydrolase encoding gene aguA (belonging to E.C. 3.5.3.12; also referred to as agmatine deiminase encoding gene), and an N-carbamoylputrescine amidohydrolase encoding gene aguB (belonging to E.C. 3.5.1.53), and optionally also an agmatinase encoding gene speB (belonging to E.C. 3.5.3.11).

Overexpression as meant herein for these additionally increased enzyme activities, can be achieved by any method known to the skilled man; for instance by increasing the translational and/or transcriptional efficiency of the respective gene, but also by any other known methods such as increasing the gene copy number, or by increasing the endogenous activity or structure of the enzymes by means of mutations, or by using deregulated enzymes. As meant in part (i) of the further preferred embodiment mentioned here above the combination of SpeA and SpeB is intended to represent any functional combination (whether in a combined fusion protein, or as separate enzyme activities) of SpeA and SpeB. In fact, this combination also might be designated as SpeAB. Part (ii) hereof represents, that in such combinations of SpeA and SpeB, the SpeB-part itself may be replaced by any functional combination (whether in a combined fusion protein, or as separate enzyme activities) of AguA and AguB.

Janowitz et al., FEBS Letters 544 (2003), 258-261, have described that agmatine deiminase AguA is involved in the arginine decarboxylase pathway in higher plants. It is further known from Nakada et al., Microbiology, 149 (2003), 707-714, that the conversions catalyzed by SpeB also can be catalyzed by enzymes occurring in plants, namely by the combined action of agmatine deiminase AguA and N-carbamoylputrescine amidohydrolase AguB. Accordingly, instead of, or even in combination with, SpeB in the context of the present invention also AguA and AguB can be used. Sources for such aguA and aguB genes could be *Arabidopsis*

*thaliana* and *Lycopersicon esculentum*, but comparable genes can be found in mutants of *Pseudomonas aeroginosa*.

It will be clear, that—in the context of the present invention—any gene being homologous with any of the genes coding for the abovementioned arginine decarboxylases, respectively agmatinases, or agmatine iminohydrolases or N-carbamoylputrescine amidohydrolases, and coding for such respective enzymes having arginine decarboxylase (respectively agmatinase, or agmatine iminohydrolase or N-carbamoylputrescine amidohydrolase) activity sufficiently comparable to the respective enzymes—as the case may be—is to be considered an equivalent thereof and suitable in this further preferred embodiment of the process of the invention. Such equivalent genes suitably can be obtained by means of any suitable cloning strategy known to the skilled man, for instance, by the methods described in the experimental part hereof. Alternatively, such equivalent genes also can be obtained by purposive construction.

Accordingly, in this preferred embodiment of the process of the present invention, also additional combinations of overexpressed genes are being used, namely genes encoding for (i) arginine decarboxylase and agmatinase, or (ii) arginine decarboxylase and agmatine iminohydrolase and N-carbamoylputrescine amidohydrolase, and optionally agmatinase.

In this further preferred embodiment of the invention, the overexpressed arginine decarboxylase encoding gene is preferably an arginine decarboxylase gene speA originating from one of the genera selected from the group consisting of *Escherichia*, *Shigella*, *Salmonella*, *Yersinia*, *Pasteurella*, and *Neisseria*. More preferably, the overexpressed arginine decarboxylase encoding gene is an arginine decarboxylase gene speA originating from one of the species selected from the group consisting of *Escherichia coli*, *Shigella flexneri*, *Salmonella enterica*, *Yersinia pestis*, *Pasteurella multocida*, and *Neisseria meningitidis*.

According to the present invention, in particular, all arginine decarboxylases can be used that have sufficient, i.e. at least 30%, more preferably at least 45%, and most preferably at least 65%, identity with the arginine decarboxylase from the *E. coli* reference enzyme, and are capable of catalyzing the arginine decarboxylation reaction. Many arginine decarboxylases are known having such relatively high level of identity with the *E. coli* reference enzyme.

In this further preferred embodiment of the invention, the overexpressed agmatinase encoding gene is an agmatinase gene speB originating from one of the genera selected from the group consisting of *Escherichia*, *Salmonella*, *Proteus*, *Photorhabdus*, *Vibrio*, and *Neisseria*. More preferably, the overexpressed agmatinase encoding gene is an agmatinase gene speB originating from one of the species selected from the group consisting of *Escherichia coli*, *Salmonella enterica*, *Proteus mirabilis*, *Photorhabdus luminescens*, *Vibrio cholerae*, and *Neisseria meningitidis*.

According to the present invention, in particular, all agmatinases can be used that have sufficient, i.e. at least 30%, more preferably at least 45%, and most preferably at least 60%, identity with the agmatinase from the *E. coli* reference enzyme, and are capable of catalyzing the agmatinase reaction. Many agmatinases are known having such relatively high level of identity with the *E. coli* reference enzyme.

In this further preferred embodiment of the invention, moreover, the overexpressed agmatine iminohydrolase encoding gene and/or the overexpressed N-carbamoylputrescine amidohydrolase encoding gene is preferably an agmatine iminohydrolase gene aguA and/or an N-carbamoylputrescine amidohydrolase gene aguB originating from one of the genera selected from the group consisting of *Pseudomonas*, *Streptococcus*, *Streptomyces*, *Azotobacter*, *Arabidopsis*, *Novosphingobium*, and *Bacillus*. More preferably, the overexpressed agmatine iminohydrolase encoding gene and/or the overexpressed N-carbamoylputrescine amidohydrolase encoding gene is an agmatine iminohydrolase gene aguA and/or an N-carbamoylputrescine amidohydrolase gene aguB originating from one of the species selected from the group consisting of *Pseudomonas aeruginosa*, *Streptococcus mutans*, *Streptomyces avermitilis*, *Azotobacter vinelandii*, *Arabidopsis thaliana*, *Novosphingobium aromaticivorans*, and *Bacillus cereus*.

According to the present invention, in particular, all agmatine iminohydrolases and/or N-carbamoylputrescine amidohydrolases can be used that have sufficient, i.e. at least 30%, and most preferably at least 40%, identity with the agmatine iminohydrolase and/or the N-carbamoylputrescine amidohydrolase from the *Pseudomonas* reference enzyme, and are capable of catalyzing the agmatine iminohydrolase, respectively the N-carbamoylputrescine amidohydrolase reaction. Many agmatine iminohydrolases and/or the N-carbamoylputrescine amidohydrolases are known having such relatively high level of identity with the *Pseudomonas* reference enzyme.

It is preferred, that the process according to the invention is being carried out whilst ensuring an increased intracellular level of ornithine. This can, for instance, be achieved by externally feeding of ornithine.

The process of the invention may be carried out in any suitable host organism. The hosts may be selected from the groups of production organisms (or cells) generally known to the skilled man in biosynthesis. Such organisms may be from eukaryotic origin, or—as is more preferred—from prokaryotic origin. Eukaryotic cells, for instance, can be cells from plants and fungi, and from various other groups, which other groups collectively are referred to as "Protista".

It is particularly preferred, that the process according to the invention is carried out in a host organism selected from the group consisting of *Saccharomyces* sp., *Bacillus* sp., *Corynebacterium* sp., *Escherichia* sp. and *Pichia* sp.

In the process of the invention, it is especially preferred that the microorganism to be used as a host is able to produce the amino acids ornithine and/or arginine. For most natural microorganisms this requirement is fulfilled because usually such capability is available in all wild type strains, since arginine represents an essential amino acid.

Of these species, *Escherichia* sp. are preferred because they are easy to handle by genetic manipulation in order to provide strains with the desired overexpressed enzyme activities. Moreover, *Escherichia* sp. already in nature contain almost each of the abovementioned enzyme activities (i.e. apart from the agu genes from plants), so that most of the overexpressed genes can be used as homologous genes. Also, *Corynebacterium* sp. (though lacking a natural ornithine decarboxylase) is particularly preferred because it is a suitable glutamate production strain that can be handled easily in fermentation processes.

In the process of the present invention glutamate is a very suitable precursor. Accordingly, the process is preferably being carried out in a host strain capable of formation of glutamate (for instance, *Corynebacterium glutamicum*).

Best results are being achieved when the process according to the invention it is carried out in a host organism from the group consisting of *Saccharomyces cerevisiae*, *Corynebacterium* sp. and *Escherichia* sp. wherein, apart from the activity of an ornithine decarboxylase, arginine decarboxylase and at least agmatinase or agmatine iminohydrolase and N-carbamoylputrescine amidohydrolase enzyme activities is being present in the host microorganism at an increased activity level as compared with the native level of the said enzyme activity is homologous to the host microorganism.

It will be clear that the process of the invention is preferably carried out under reaction conditions that are also usual as fermentation conditions. The process, therefore can be carried out batch-wise, but also—if so desired—fed-batch. It may be convenient to ensure that the organism used as host organism has, or is provided with, a suitable exporter system for the 1,4-diaminobutane formed: Preferably such exporter system is a native one.

The present invention, of course, also encompasses all vectors, plasmids and hosts carrying, at an increased level of activity, one or more of the aforementioned enzyme activities according to the attached claims.

The invention will now be elucidated by means of some experimental results, which by no means are intended to limit the scope of the invention.

EXPERIMENTAL PART

General Procedures

Standard procedures were applied for all DNA manipulations (Sambrook, J. et al., (1989), *Molecular cloning: a laboratory manual*, 2nd Ed., Cold Spring Harbor Laboratory Press, Cold Spring Harbor, N.Y.). DNA was amplified from chromosomal DNA of *E. coli* LJ 110 (Zeppenfeld, et al., (2000), *J Bacteriol*. 182, 4443-4452) if not indicated otherwise. PCR amplification was performed using the proofreading enzymes SAWADY Pwo-DNA-Polymerase (Peqlab Biotechnologie GmbH, Erlangen, Germany) or Platinum Pfx DNA Polymerase (Invitrogen, Karlsruhe, Germany) following the manufacture's protocol, whereas the verification of the constructed strains was carried out by colony PCR utilizing the Taq polymerase READYMIX (Sigma, Taufkirchen, Germany). Restriction sites for subsequent cloning as well as further mutations were introduced with oligonucleotides purchased from MWG-Biotech (Ebersberg, Germany). DNA fragments were purified with the MinElute Gel Extraction Kit (Qiagen, Hilden, Germany) following the manufacture's protocol. Preparation of Plasmid DNA was Accomplished by the Utilization of Qiaprep Spin Miniprep Kit (Qiagen, Hilden, Germany). Verification of the constructed plasmids was carried out by restriction analysis and subsequent sequencing (Agowa, Berlin, Germany).

Construction of Plasmids (i) Construction of the Plasmid pDAB3 (pJF119EH-speC$_{nRBS}$)

The (constitutive, biosynthetic) ornithine decarboxylase encoding gene speC of *E. coli* LJ110 (Zeppenfeld, et al., see general procedures) was cloned into the expression vector pJF 119EH (Fürste, J. P. et al. (1986), Gene 48, 119-131), allowing a strong gene expression based on the transcriptional control under the isopropyl-β-D-thiogalactopyranoside (IPTG) inducible tac promotor and the lac repressor system (lacQ). Therefore, the coding gene speC was cloned with original RBS, start and stop codon.

The 2235 bp speC$_{nRBS}$-containing DNA fragment was amplified from chromosomal DNA of *E. coli* LJ110 (accession number AE000379; nucleotides 2650-4867) using the following oligonucleotides:

[SEQ ID: No. 1]
5'-GAG C*TC* TAG ACC AGT TTG ACC CAT ATC T-3'
(mutations in bold, XbaI restriction site in italics)
and

[SEQ ID: No. 2]
5'-TTT T*GC* ATG CTT ACT TCA ACA CAT AAC CGT AC-3'
(mutations in bold, SphI restriction site in italics).

After terminal modification with the endonucleases XbaI and SphI, the PCR product was ligated into plasmid pJF119EH, which was cut in the same manner. After transformation in *E. coli* DH5α cells (Invitrogen, Karlsruhe, Germany), transformants were selected on LB agar plates containing 100 mg/l ampicillin. After preparation, the verification of the obtained plasmid pDAB3 (pJF 119EH-speC$_{nRBS}$, 7491 bp) was carried out by restriction analysis and subsequent sequencing.

(ii) Construction of the Plasmid pDAB4 (pJF119EH-speC$_{aRBS}$)

The (constitutive, biosynthetic) ornithine decarboxylase encoding gene speC of *E. coli* LJ110 (Zeppenfeld, et al., see general procedures) was cloned into the expression vector pJF119EH (Fürste, J. P. et al. (1986), Gene 48, 119-131), allowing a strong gene expression based on the transcriptional control under the isopropyl-β-D-thiogalactopyranoside (IPTG) inducible tac promotor and the lac repressor system (lacQ). Therefore, the coding gene speC was cloned with original start and stop codon. Since, no conserved ribosomal binding site (RBS) could be determined for speC utilizing in silico studies, the RBS, located 7 bp upstream of the speC start codon, was adapted to the consensus sequence of *E. coli* by site-directed mutagenesis.

The 2235 bp speC$_{aRBS}$-containing DNA fragment was amplified from chromosomal DNA of *E. coli* LJ110 (accession number AE000379; nucleotides 2650-4867) using the following oligonucleotides:

[SEQ ID: No. 3]
5'-GAG C*TC* TAG ACC AGT TTG AGG AAT ATC T-3'
(mutations in bold, XbaI restriction site in italics)
and

[SEQ ID: No. 2]
5'-TTT T*GC* ATG CTT ACT TCA ACA CAT AAC CGT AC-3'
(mutations in bold, SphI restriction site in italics).

After terminal modification with the endonucleases XbaI and SphI, the PCR product was ligated into plasmid pJF119EH, which was cut in the same manner. After transformation in *E. coli* DH5α cells (Invitrogen, Karlsruhe, Germany), transformants were selected on LB agar plates containing 100 mg/l ampicillin. After preparation, the verification of the obtained plasmid pDAB4 (pJF119EH-speC$_{aRBS}$, 7491 bp) was carried out by restriction analysis and subsequent sequencing.

(iii) Construction of the Plasmid pDAB2 (pJF119EH-speF)

The (inducible, biodegradative) ornithine decarboxylase encoding gene speF of *E. coli* LJ110 (Zeppenfeld, et al., see general procedures) was cloned into the expression vector pJF119EH (Fürste, J. P. et al. (1986), Gene 48, 119-131). This vector allows a high-level protein production based on the transcriptional control of cloned genes under the isopropyl-β-D-thiogalactopyranoside (IPTG) inducible tac promotor and the lac repressor system (lacQ). For construction of the expression plasmid pDAB2 (pJF119EH-speF) the coding gene speF was cloned with original RBS (ribosomal binding site), start and stop codon.

The 2247 bp speF-containing DNA fragment was amplified from chromosomal DNA of *E. coli* LJ110 (accession number AE000172; nucleotides 10242-12468) using the following oligonucleotides:

[SEQ ID: No. 4]
5'-GAC CTG CTG GTA CCT AAA ATA AAG AGA TGA AA-3'
(mutations in bold, KpnI restriction site in italics)
and

[SEQ ID: No. 5]
5'-TCG ATC TAG ACT GAC TCA TAA TTT TTC CCC-3'
(mutations in bold, XbaI restriction site in italics).

The fragment was terminally modified with the restriction endonucleases KpnI and XbaI and ligated into the expression vector pJF119EH, which was cut in the same manner. After transformation in *E. coli* DH5α cells (Invitrogen, Karlsruhe, Germany), transformants were selected on LB agar plates containing 100 mg/l ampicillin. After preparation, the obtained plasmid pDAB2 (pJF119EH-speF, 7502 bp) was verified by restriction analysis and subsequent sequencing.

(iv) Construction of the Plasmid pDAB7 (pJF119EH-speAB)

The arginine decarboxylase encoding gene speA as well as speB coding for the agmatinase of *E. coli* LJ110 (Zeppenfeld, et al., see general procedures) were cloned into the expression vector pJF119EH (Fürste, J. P. et al. (1986), *Gene* 48, 119-131) allowing a high-level protein production based on the transcriptional control of cloned genes under the isopropyl-β-D-thiogalactopyranoside (IPTG) inducible tac promotor and the lac repressor system (lac$^Q$). This way, the original operon structure of the genes as well as RBS, start and stop codon were maintained.

The 3079 bp speAB-containing DNA fragment was amplified from chromosomal DNA of *E. coli* LJ110 (accession number AE000377; nucleotides 1190-4247) using the following oligonucleotides:

[SEQ ID: No.6]
5'-ACA CTT TCT AGA ATA ATT TGA GGT TCG CTA TG-3'
(mutations in bold, XbaI restriction site in italics)
and

[SEQ ID: No.7]
5'-CAT GGC ATG CGG TGC TTA CTC G-3'
(mutations in bold, SphI restriction site in italics).

After terminal modification with the restriction endonucleases XbaI and SphI, the DNA fragment was ligated into the expression plasmid pJF119EH, which was cut likewise. After transformation in *E. coli* DH5α cells (Invitrogen, Karlsruhe, Germany), transformants were selected on LB agar plates containing 100 mg/l ampicillin. After preparation, the verification of the obtained plasmid pDAB7 (pJF 119EH-speAB, 8339 bp) was carried out by restriction analysis and subsequent sequencing.

(v) Construction of the Plasmid pDAB8 (pJF119EH-speF-speAB)

In order to allow in-parallel production of the ornithine decarboxylase SpeF, the arginine decarboxylase SpeA and the agmatinase SpeB, the speAB genes of *E. coli* LJ110 (Zeppenfeld, et al., see general procedures) were cloned into the speF-expression vector pDAB2 (see iii)).

By digestion of the plasmid pDAB7 (see iv)) with the restriction endonucleases XbaI and SphI, the 3067 bp comprising speAB gene-operon was separated and ligated into the speF containing plasmid pDAB2 (see (iii)), which was cut in the same manner. After transformation in *E. coli* DH5α cells (Invitrogen, Karlsruhe, Germany), transformants were selected on LB agar plates containing 100 mg/l ampicillin. After preparation, the obtained plasmid pDAB8 (pJH119EH-speFAB, 10547 bp) allowing the in-parallel production of SpeFAB was verified by restriction analysis.

EXAMPLE 1

Improvement of DAB Production by Overexpression of Ornithine Decarboxylase Encoding Genes with Increased Translational and/or Transcriptional Efficiency

EXAMPLE 1.1

Production of 1,4-butanediamine Via the Overproduction of Ornithine Decarboxylases (Shake Flask)

The influence of overexpression of ornithine decarboxylase encoding genes speF or speC (with increased translational and/or transcriptional efficiency) on DAB production was investigated within the *E. coli* host strain LJ110 (Zeppenfeld, et al., see general procedures) carrying the plasmid pDAB2 (see (iii)), or pDAB3 (see (i)), or pDAB4 (see (ii)).

These strains were tested in shake flask experiments utilizing minimal salt medium consisting of $MgSO_4.7H_2O$ (300 mg/l), $CaCl_2.2H_2O$ (15 mg/l), $KH_2PO_4$ (3 g/l), $K_2HPO_4$ (12 g/l), NaCl (100 mg/l), $(NH_4)_2SO_4$ (5 g/l), Na citrate.$3H_2O$ (1 g/l), $FeSO_4.7H_2O$ (75 mg/l), thiamine.HCl (vitamin B1) (5 mg/l) as well as the trace elements $Al_2(SO_4)_3.18H_2O$ (3 mg/l), $CoCl_2.6H_2O$ (1.05 mg/l), $CuSO_4.5H_2O$ (3.75 mg/l), $H_3BO_3$ (0.75 mg/l), $MnCl_2.4H_2O$ (30 mg/l), $Na_2MoO_4.2H_2O$ (4.5 mg/l), $NiSO_4.6H_2O$ (3 mg/l) and $ZnSO_4.7H_2O$ (22.5 mg/l). A stock solution of glucose (500 g/l) was autoclaved separately and added to the sterilized medium up to a final concentration of 10 g/l.

A preculture of minimal salt medium containing 100 mg/l ampicilline was inoculated with 1-5 µl/ml stock solution and incubated at 33° C., 180 rpm for 16 h up to an $OD_{620}$ of 2.5 ml of this culture was subsequently used for inoculation of the main culture consisting of 50 ml of the same medium, which was incubated for 24 h at 33° C. and 180 rpm. Since the cells reached an $OD_{620nm}$ of 1.5 (after ~7 h), gene expression was induced by the addition of 50 µM IPTG.

In order to observe the time-dependent DAB production, samples were taken at different time points during cultivation. After separation of the cells utilizing centrifugation, diluted supernatant was analyzed by HPLC. Here, the contained amines were detected as ortho-phthaldialdehyde (OPA) derivatives at 230 nm on a Hewlett-Packard 1100 Series instrument, using a $C_{18}$-reverse phase column (Nucleosil 120-5 $C_{18}$, Macherey & Nagel, Düren, Germany) equilibrated to 50% buffer B (buffer A, 0.1 M sodium acetate pH 7.2; buffer B methanol). For separation, the following gradient was applied: 1-7 min linear gradient from 50% to 75% buffer B with a flow rate of 0.5 ml/min, 7-13 min 75% to 85% buffer B with a flow rate of 0.5 ml/min, 13-14.5 min 85% to 50% buffer B with a low rate of 1 ml/min, 14.5-17 min 50% buffer B with a flow rate of 1 ml/min and 17-20 min at 50% buffer B with a flow rate of 0.5 ml/min.

By the utilization of standard substances for calibration, the following DAB concentrations could be determined (see Table 1) and verified by NMR spectroscopy.

TABLE 1

DAB formation utilizing ODC overproduction in *E. coli*

| Strain used | Gene expressed | DAB concentration [mg/l] | Remarks |
|---|---|---|---|
| LJ110 pDAB2 | speF | 869 | IPTG induction; „RBS |
| LJ110 pDAB3 | speC$_{nRBS}$ | ~50 | IPTG induction; „RBS |
| LJ110 pDAB4 | speC$_{aRBS}$ | 715 | Adapted RBS + IPTG induction |

EXAMPLE 1.2

Production of 1,4-butanediamine Via the Overproduction of Ornithine Decarboxylase within Fed Batch (2 l) Cultivation The potential of fermentative dab production under fed batch conditions was investigated by the utilization of the high-level DAB producer strain LJ110 pDAB2 within a labfors bioreactor (Infors, Einsbach, Germany). Since, the DAB producing strain is not amino acid dependent for its growth, a developed protocol for phosphate limited cultivation was applied in order to restrict the cell growth. Therefore, a phosphate limited minimal salt medium was used consisting of MgSO$_4$.7H$_2$O (3 g/l), CaCl$_2$.2H$_2$O (15 mg/l), KH$_2$PO$_4$ (400 mg/l), NaCl (1 g/l), (NH$_4$)$_2$SO$_4$ (5 g/l) as well as the trace elements Al$_2$(SO$_4$)$_3$.18H$_2$O (3 mg/l), CoCl$_2$.6H$_2$O (1.05 mg/l), CuSO$_4$.5H$_2$O (3.75 mg/l), H$_3$BO$_3$ (0.75 mg/l), MnCl$_2$.4H$_2$O (30 mg/l), Na$_2$MoO$_4$.2H$_2$O (4.5 mg/l), NiSO$_4$.6H$_2$O (3 mg/l) and ZnSO$_4$.7H$_2$O (22.5 mg/l). After autoclaving, Na citrate.3H$_2$O (1.5 g/l), FeSO$_4$.7H$_2$O (112.5 mg/l), thiamine.HCl (vitamin B1) (7.5 mg/l), ampicilline (100 mg/l) and glucose (10 g/l) was added under sterile conditions into the bioreactor.

A preculture of minimal salt medium (see 1.1) containing 100 mg/l ampicilline was inoculated with 1-5 µl/ml stock solution and incubated at 33° C., 180 rpm for 16 h up to an optical density at 620 nm of 2. Following, this culture was subsequently used for 1:10 inoculation of the main culture consisting of 2 l phosphate limited minimal salt medium. During cultivation, the temperature was kept constant at 33° C. and the pH was controlled to 6.8±0.1 by the addition of 5 N KOH. During growth, a stable agitation speed of 1500 rpm was used. In order to avoid oxygen limitation, the gas flow into the vessel was increased from 2.5-10l/min during cultivation. Antifoam Dehysan was added as needed.

The cells were induced with 50 µM IPTG at an OD$_{620}$ of 5 followed by a combined glucose (500 g/l)/ammonia sulfate (200 g/l) feed, whereas the feeding rate was adapted in order to receive stable concentrations of 10 g/l glucose and 1.5 g/l ammonia. Two hours after induction, phosphate feed consisting of 18 g/l KH$_2$PO$_4$ with a feeding rate of 7 ml/h was started for 8 h. This way, cell growth could be restricted to an OD$_{620}$ of ~50.

In order to observe the time-dependent DAB production, samples were taken at different time points during cultivation. After separation of the cells utilizing centrifugation, supernatant was analyzed by HPLC (see 1.1) and a DAB amount of 5.1 g/l (0.403 g/gBDW; BDW means Biomass Dry Weight) was determined and verified by NMR spectroscopy.

EXAMPLE 2

Production of 1,4-butanediamine within Batch Starting from Ornithine as Well as Arginine (Shake Flask)

For demonstrating further improvement of DAB formation starting from ornithine as well as arginine, the influence of combined overproduction of the ornithine decarboxylase SpeF (with increased transcriptional efficiency), the arginine decarboxylase SpeA and the agmatinase SpeB was investigated.

Therefore, shake flask cultivations were carried out in minimal salt medium (see 1.1) by the utilization of the *E. coli* host strain LJ110 (Zeppenfeld, et al., see general procedures) carrying the plasmid pDAB8 (see (v)). Therefore, a preculture of minimal salt medium containing 100 mg/l ampicilline was inoculated with 1-5 µl/ml stock solution and incubated at 33° C., 180 rpm for 16 h up to an optical density at 620 nm of 2.5 ml of this culture was subsequently used for inoculation of the main culture consisting of 50 ml of the same medium, which was incubated for 24 h at 33° C. and 180 rpm. Since the cells reached an OD$_{620nm}$ of 1.5 (after ~7 h), gene expression was induced by the addition of 10 µM IPTG.

In order to observe the time-dependent DAB production, samples were taken at different time points during cultivation. After separation of the cells utilizing centrifugation, the supernatant was analyzed by HPLC (see 1.1). By the utilization of standard substances for calibration, the following DAB concentrations could be determined (see Table 3).

TABLE 2

DAB formation starting from ornithine as well as arginine in *E. coli*

| d strain | expressed genes | DAB concentration [mg/l] |
|---|---|---|
| LJ110 pDAB8 | speFAB | 1025 |

The invention claimed is:

1. A method for production of 1,4-butanediamine (DAB) in a fermentation process by a genetically modified *Escherichia coli* (*E. coli*) bacterium which has the ability to produce ornithine decarboxylase (ODC), wherein said *E. coli* bacterium has been modified to enhance an activity of ODC, the method comprising:
   (i) transforming said *E. coli* bacterium with a plasmid comprising an ornithine decarboxylase speF gene from Enterobacteracea family under the control of an isopropyl-β-D-thiogalactopyranoside (IPTG) inducible strong promoter,
   (ii) culturing the modified *E. coli* bacterium of (i) in a glucose and mineral salt containing fermentation broth to allow overexpression of the ornithine decarboxylase speF, and
   (iii) collecting the 1,4-butanediamine (DAB) produced and excreted by the modified *E. coli* bacterium into the fermentation broth, wherein the accumulation of DAB into the fermentation broth is at least 715 mg/L.

2. A method for production of 1,4-butanediamine (DAB) in a fermentation process by a genetically modified *Escherichia coli* (*E. coli*) bacterium which has the ability to produce ornithine decarboxylase (ODC), wherein said *E. coli* bacterium has been modified to enhance an activity of ODC, the method comprising:
   (i) transforming said *E. coli* bacterium with a plasmid comprising an ornithine decarboxylase speC gene from Enterobacteracea family under the control of an isopropyl-β-D-thiogalactopyranoside (IPTG) inducible strong promoter,
   (ii) culturing the modified *E. coli* bacterium of (i) in a glucose and mineral salt containing fermentation broth to allow overexpression of the ornithine decarboxylase speC, and
   (iii) collecting the 1,4-butanediamine (DAB) produced and excreted by the modified *E. coli* bacterium into the fermentation broth, wherein the accumulation of DAB into the fermentation broth is at least 715 mg/L.

* * * * *